(12) United States Patent
Subramanian et al.

(10) Patent No.: US 7,298,818 B2
(45) Date of Patent: Nov. 20, 2007

(54) METHODOLOGIES FOR NON-DESTRUCTIVE QUANTIFICATION OF THERMAL BARRIER COATING TEMPERATURES ON SERVICE RUN PARTS

(75) Inventors: Ramesh Subramanian, Oviedo, FL (US); Anand A. Kulkarni, Orlando, FL (US)

(73) Assignee: Siemens Power Generation, Inc., Orlando, FL (US)

( * ) Notice: Subject to any disclaimer, the term of this patent is extended or adjusted under 35 U.S.C. 154(b) by 80 days.

(21) Appl. No.: 11/243,370

(22) Filed: Oct. 4, 2005

(65) Prior Publication Data

US 2007/0076845 A1   Apr. 5, 2007

(51) Int. Cl.
  *G01B 15/06*   (2006.01)
(52) U.S. Cl. ................. 378/58; 250/390.02; 250/358.1
(58) Field of Classification Search ................. 378/51, 378/54, 58, 70–90, 901; 250/390.04, 390.06, 250/390.09, 390.02, 358.1; 702/27, 28
  See application file for complete search history.

(56) References Cited

U.S. PATENT DOCUMENTS

| | | | |
|---|---|---|---|
| 5,400,381 | A | 3/1995 | Steude et al. |
| 5,567,051 | A | 10/1996 | Annati et al. |
| 6,365,281 | B1 | 4/2002 | Subramanian et al. |
| 6,804,622 | B2 | 10/2004 | Bunker et al. |
| 6,869,703 | B1 | 3/2005 | Spitsberg et al. |
| 6,873,680 | B2 | 3/2005 | Jones |
| 2002/0076097 | A1 | 6/2002 | Vaidyanathan |
| 2002/0110176 | A1 | 8/2002 | Sun et al. |

(Continued)

OTHER PUBLICATIONS

Anand A. Kulkarni, Allen Goland, Herbert Herman, Andrew J. Allen, Jan Ilavsky, Gabrielle G. Long, Francesco De Carlo; "Advanced Microstructural Characterization of Plasma—Sprayed Zirconia Coatings Over Extended Length Scales"; In press J. Therm. Spray. Technol., (Jun. 2005); 22 pages.

(Continued)

*Primary Examiner*—Jurie Yun

(57) ABSTRACT

Methodologies for non-destructively inspecting and characterizing micro-structural features in a thermal barrier coating (TBC) on a component, wherein the micro-structural features define pores and cracks, if any, in the TBC. The micro-structural features having characteristics at least in part based on a type of process used for developing the TBC and affected by operational thermal loads to which a TBC is exposed. In one embodiment, the method allows detecting micro-structural features in a TBC, wherein the detecting of the micro-structural features is based on energy transmitted through the TBC, such as may be performed with a micro-feature detection system 20. The transmitted energy is processed to generate data representative of the micro-structural features, such as may be generated by a controller 26. The data representative of the micro-structural features is processed (e.g., by a processor 30) to determine at least one of the following: volumetric porosity information for the TBC and variation in the characteristics of the micro-structural features over a thickness of the TBC. Based on the results of the data processing, information is generated regarding at least one of the following: a present condition of the thermal barrier coating and a future likely condition of the thermal barrier coating. In another embodiment, one can estimate a level of thermal load to which the thermal barrier coating has been exposed.

18 Claims, 3 Drawing Sheets

U.S. PATENT DOCUMENTS

2003/0106376 A1    6/2003    Shirzad et al.
2004/0240600 A1    12/2004   Freyer et al.

OTHER PUBLICATIONS

Anand Kulkarni, Herbert Herman, Francesco DeCarlo, Ramesh Subramanian; "Microstructural Characterization of EB-PVD Thermal Barrier Coatings Through High-Resolution Computed Microtomography", Met. Mat. Trans A, 35A, 1945 (2004); 19 pages.

Anand A. Kulkarni; "On the Porosity-Property Correlations in Thermo-Structural Coatings: Towards an Integrated Approach"; Ph. D Thesis, State University of New York, Stony Brook; Dec. 2002; 200 pages.

METHODOLOGIES FOR NON-DESTRUCTIVE QUANTIFICATION OF THERMAL BARRIER COATING TEMPERATURES ON SERVICE RUN PARTS

RELATED APPLICATIONS

This application is related to patent application Ser. No. 11/242,664, titled "System and Computer Program Product For Non-Destructive Quantification Of Thermal Barrier Coating Temperatures On Service Run Parts", filed concurrently with the present application, assigned in common to the same assignee and herein incorporated by reference in its entirety.

FIELD OF THE INVENTION

The present invention is generally related to non-destructive inspection of a thermal barrier coating (TBC), and, more particularly, to a system and method for non-destructive quantification of TBC temperatures on a service-run component.

BACKGROUND OF THE INVENTION

It is known to use various superalloy materials, such as cobalt or nickel-based superalloys, for making blades, vanes and other components for power generating turbines, propulsion equipment, etc. These turbines can operate at temperatures in the range of approximately 1000 Deg. C. to approximately 1700 Deg. C. and are generally protected by a series of protective coatings. The coatings may comprise layers of metallic base coats, thermally grown oxide layers, as such layers grow in service-run components and a final ceramic thermal barrier coating ("TBC"). Long-term exposure of these ceramic coatings to the hostile, high temperature, abrasive environment in which such turbines typically operate can cause phase destabilization, sintering, microcracking, delamination and ultimately spallation within the coating layers, exposing the superalloy component and possibly resulting in rapid degradation or failure and potentially requiring costly and burdensome repairs.

BRIEF DESCRIPTION OF THE DRAWINGS

Advantages of the present invention will be more apparent from the following description in view of the following drawings wherein.

DETAILED DESCRIPTION OF THE INVENTION

Figure 1:
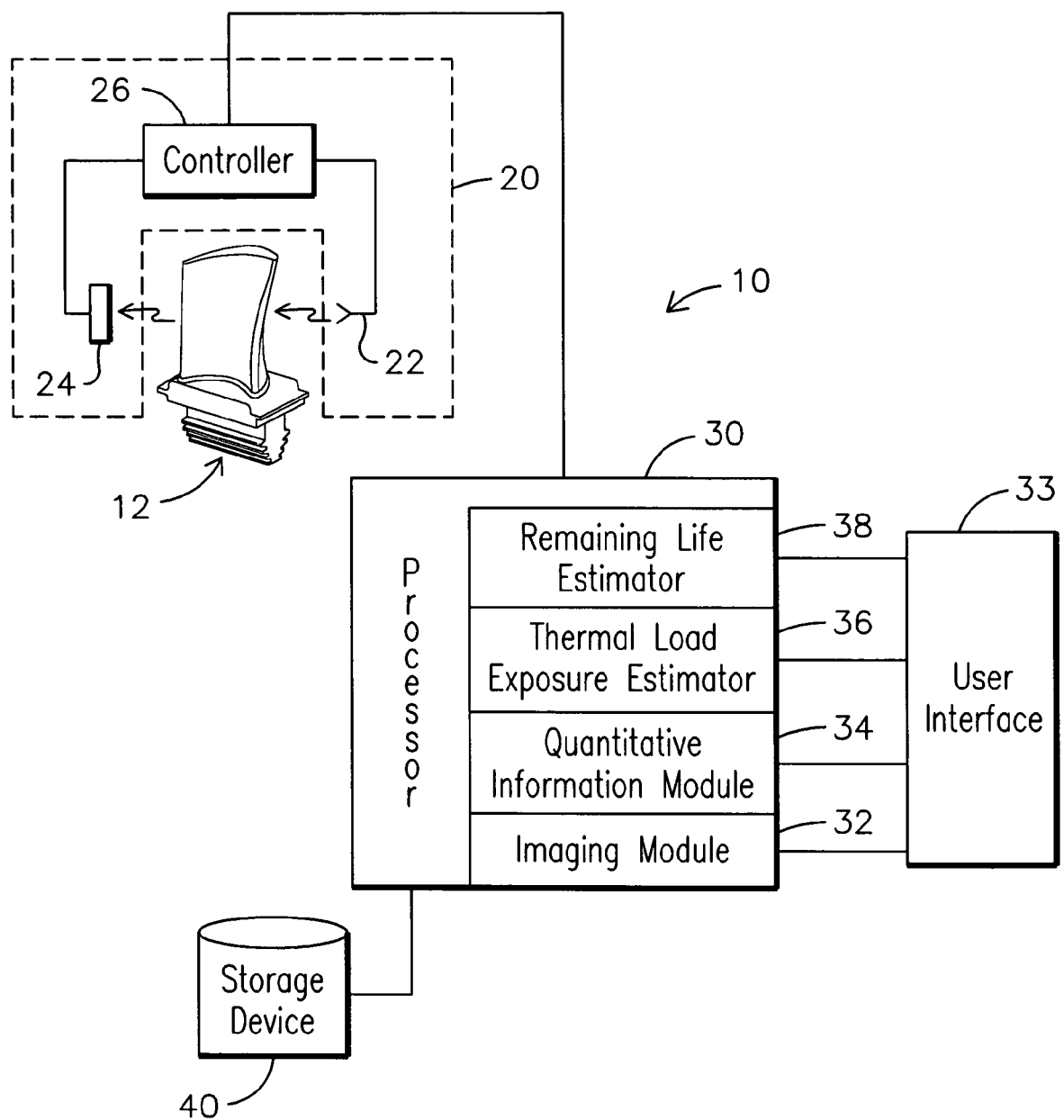
FIG. 1 is a schematic representation of an exemplary system for non-destructively inspecting and characterizing micro-structural features in a thermal barrier coating (TBC) on a component.

Before describing in detail an exemplary system in accordance with aspects of the present invention, it should be observed that such aspects reside primarily in a novel structural combination of a micro-feature detection system based on standard detection modalities, such as scattering/diffraction detection modalities, and computational modules configured to process data from such micro-feature detection system and not necessarily in the specific modality of such a detection system. Accordingly, the structure, control and arrangement of the detection system have been illustrated in the drawings by readily understandable block diagrams which show just those specific details that are considered pertinent to the present invention, so as not to burden the disclosure with superfluous details that will be readily apparent to those skilled in the art having the benefit of the description herein. Thus, any block diagram illustrations may not necessarily represent each and every structural nuance, but are primarily intended to generically illustrate the major components of the system in a convenient functional grouping, whereby aspects of the present invention may be more readily understood.

Thermal barrier coatings (TBCs) can be deposited onto blades, vanes and other components for power generating turbines, propulsion equipment, etc., using processes such as air plasma spraying (APS), electron beam physical vapor deposition, (EB PVD) or chemical vapor deposition (CVD). These processes generally produce distinctive micro-structural features in the TBC for providing thermal protection to the component. For example, in APS TBC, the deposit is developed by successive impingement and inter-bonding of a plurality of splats that result in a layered porosity predominantly parallel to the substrate where the TBC is deposited. By way of comparison, TBCs produced by EB-PVD have a columnar microstructure with elongated inter-columnar pores predominantly perpendicular to the substrate. Regardless of the specific process used for depositing the TBC, the coating can deteriorate and eventually fail when, for example, the TBC surface is exposed over a relatively long period of time to temperatures that exceed a specified design limit of the coating.

The inventors of the present invention have recognized a TBC-characterizing technique that among other innovative aspects allows estimating temperature exposure of in-service TBC components. This involves a determination of the micro-structural features of the TBC across a thickness of the TBC. For example, a determination of porosity variation across the TBC thickness may be made by generating data representative of such micro-structural features.

FIG. 1 is a schematic representation of a system 10 for non-destructively characterizing micro-structural features in a thermal barrier coating on a component 12. The micro-structural features define pores and micro-cracks that can develop in the thermal barrier coating. The micro-structural features have characteristics at least in part based on the type of process (e.g., APS or EB PVD) used for developing the thermal barrier coating.

In one exemplary embodiment, system 10 includes a micro-feature detection system 20 configured to detect the micro-structural features in the thermal barrier coating. The detection of the micro-structural features is based on energy transmitted through the coating. For example, in a detection system based on X-ray computed micro-tomography (XMT), such as may be used for 3-D imaging, an x-ray beam from an x-ray source 22 traverses the component 12, and the transmitted beam is incident on a detector 24, e.g., an array detector. The detection system 20 includes a controller 26 connected to detector 24 to acquire and process data representative of the micro-structural features. It will be appreciated that other scattering/diffraction modalities for detecting micro-features, such as Small-Angle Neutron Scattering (SANS), and Ultra-Small-Angle X-ray Scattering (USAXS), may be employed provided they are configured with sufficient energy and with the capability for extracting sufficient geometric information for non-destructively quantifying and/or visualizing the micro-structural features of the TBC on turbine parts. For readers desirous of obtaining general background information in connection with various modalities experimentally used for conducting high-energy scattering/diffraction techniques on TBCs, reference is made to a dissertation presented on December 2002 by Anand A. Kulkarni to the Graduate School of the State University of New York at Stony Brook, which dissertation is herein incorporated by reference in its entirety.

Figure 3A:
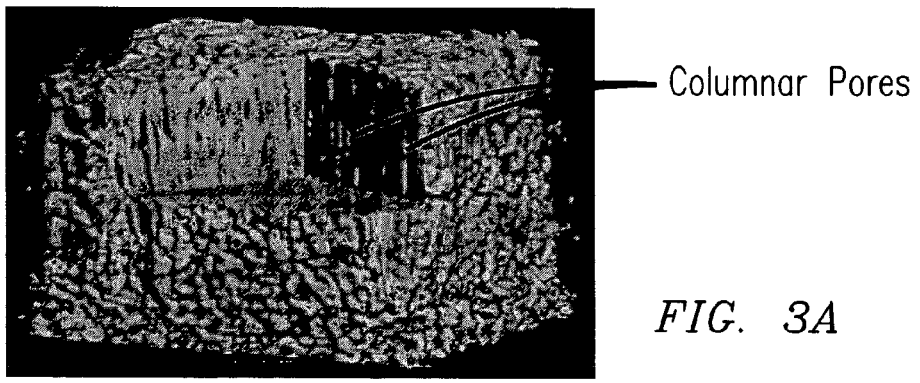
FIGS. 3A and 3B respectively illustrate three-dimensional representations of TBC microstructural features (e.g., pore morphologies and cracks that may form in the TBC) as may be generated by a system embodying aspects of the invention.
Figure 3B:
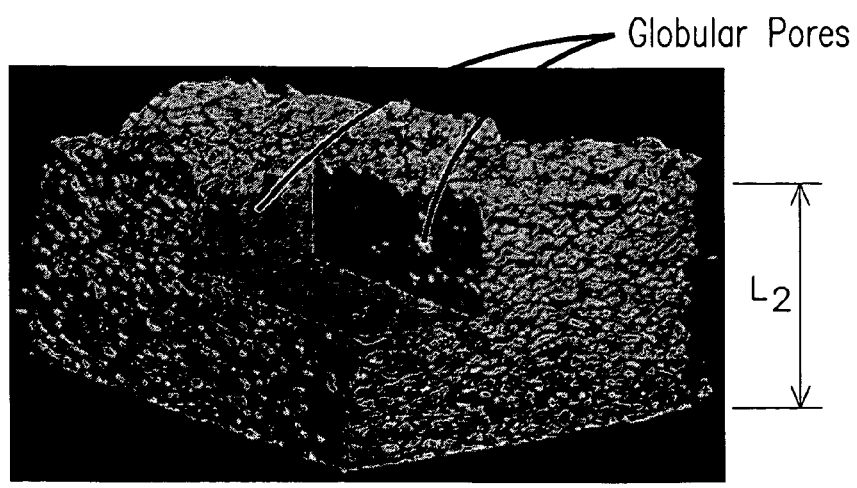

System 10 further includes a processor 30 configured to process the data representative of the micro-structural features to determine in one exemplary embodiment a volumetric porosity of the TBC and, in other cases, the variation in the characteristics of the micro-structural features over a thickness of the thermal barrier coating, or both. In one exemplary embodiment, processor 30 includes an imaging module 32 configured to form a three-dimensional image of the micro-structural features. The three-dimensional image is configured (e.g., with sufficient resolution) to enable a user to visually assess the volumetric porosity of the TBC and/or the variation in the characteristics of the micro-structural features over the thickness of the thermal barrier coating. FIGS. 3A and 3B illustrate exemplary 3D imaging representations of pore structures as may be generated by imaging module 32 to be displayed, for example, by a suitable user interface 33.

Figure 4:
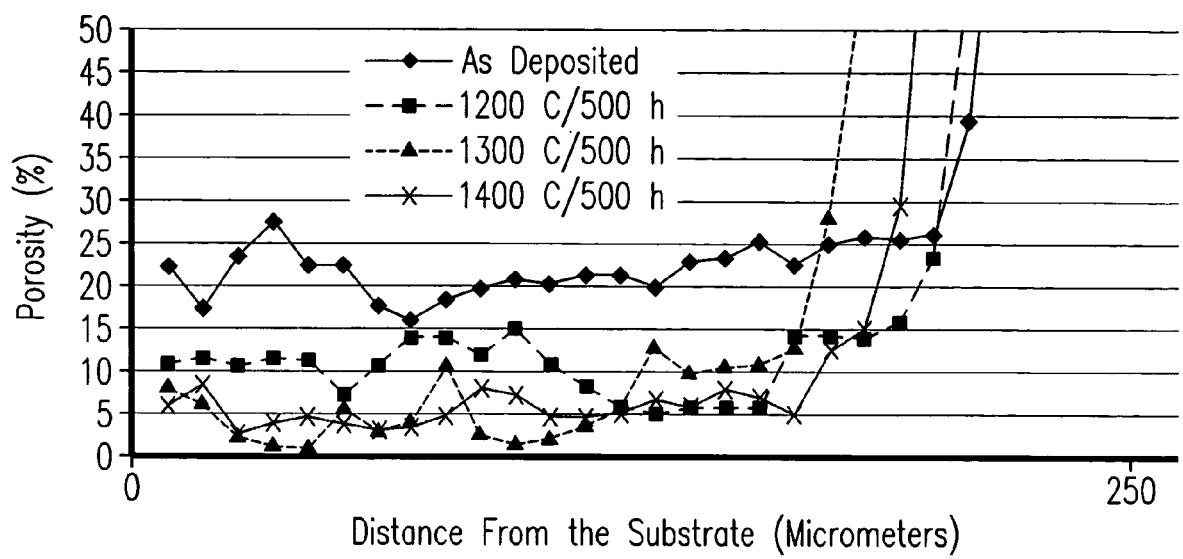
FIG. 4 is a plot as may be generated by a system embodying aspects of the present invention for quantifying changes in the microstructure (e.g., porosity) of a TBC with respect to exposure temperature of the coating.

Processor 30 may further include a quantitative information module 34 configured to quantitatively assess the volumetric porosity of the TBC and/or the variation in the characteristics of the micro-structural features over the thickness of the thermal barrier coating. FIG. 4 illustrates an exemplary plot as may be generated by quantitative information module 34 for quantifying changes in the microstructure (porosity) of TBC coatings with respect to a level of temperature exposure.

A module 36 may be configured to estimate a level of thermal load to which the thermal barrier coating has been exposed. This estimate may be based on the variation in the characteristics of the micro-structural features. Module 36 may be further configured to estimate time duration of exposure to the estimated level of thermal load. For example, the variation in the characteristics of the micro-structural features may be more pronounced the longer the duration of exposure to a given level of thermal load.

A remaining life estimator module 38 may be configured for estimating remaining life for a thermal barrier coating having been exposed to a given level of thermal load. In one exemplary embodiment a storage device 40 may be provided for storing representative data of a virgin coating. In this embodiment, module 38 may be configured to relate data representative of a TBC having been exposed to a given level of thermal load relative to the data representative of the virgin coating in order to make an estimate of the remaining life for the TBC.

Figure 2:
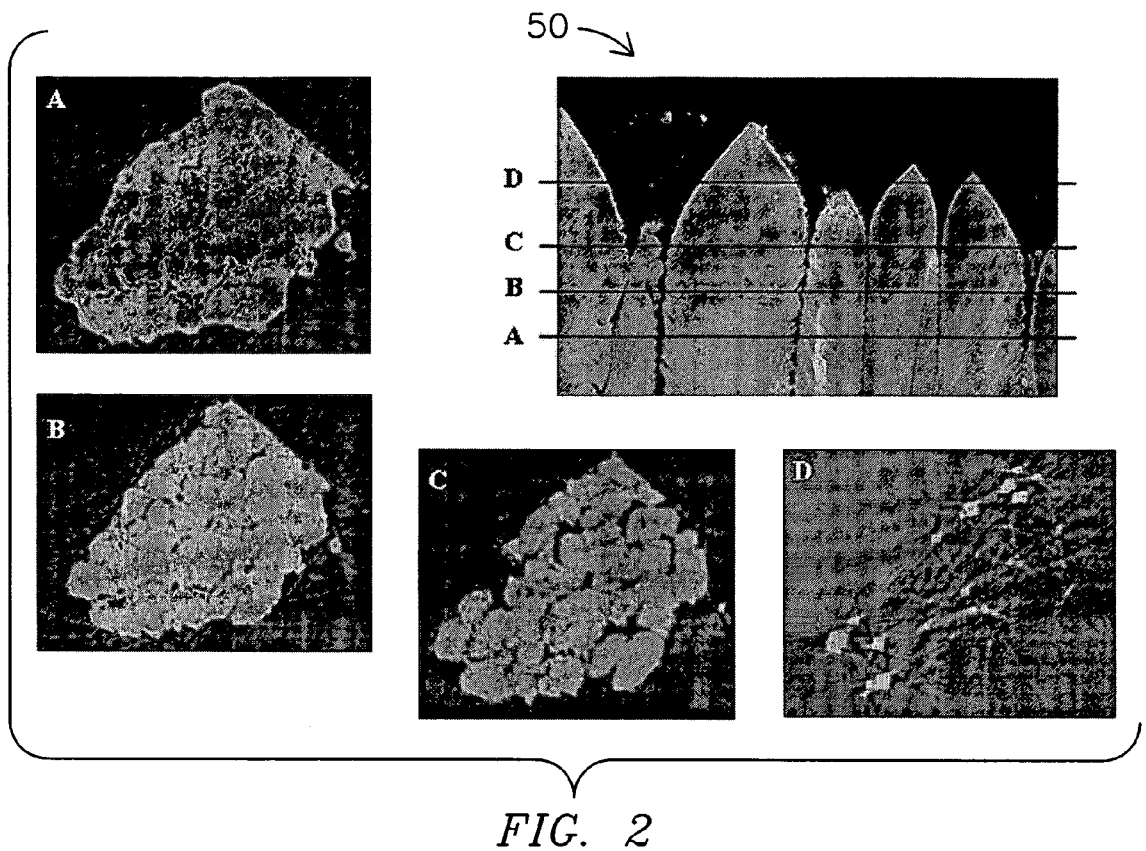
FIG. 2 shows exemplary sectional views along a thickness of a TBC as may be generated with a micro-feature detection system based on X-ray computed micro-tomography (XMT).

FIG. 2 shows exemplary graphical results obtained with a detection system based on X-ray computed micro-tomography (XMT). More particularly, FIG. 2 illustrates four reconstructed sectional images A, B, C and D of corresponding individual slices (as represented by lines A, B, C and D) along the thickness of a TBC specimen as shown in a graph 50 obtained with a Scanning Electron Microscope (SEM). It will be appreciated that the reconstructed sectional images A, B and C show exemplary variation in intercolumnar spacing as a function of thickness, and more specifically show the intercolumnar spacing to be increasing towards the top of the coating. Sectional image D essentially shows the tip of the columns.

FIGS. 3A and 3B illustrate exemplary TBC microstructural features (e.g., pore morphologies) in respective 3D representations, wherein FIG. 3A illustrates columnar pore structures in a TBC deposited by electron beam physical vapor deposition (EB PVD), and FIG. 3B illustrates globular pore structures in a TBC deposited by air plasma spraying (APS). By way of example and not of limitation, a dimension indicated by line $L_2$ may range from about 200 μm to about 250 μm in the TBC volume being inspected.

FIG. 4 is a plot for quantifying changes that may occur in the microstructure (porosity) of TBCs with respect to exposure temperature. It was observed that significant micro-structural changes can occur in the TBCs upon exposure to increasing temperatures. This may be due to increased sintering kinetics/diffusion. It was also observed that sintering/column bridging leads to reduction of porosity and in turn to loss of strain tolerance. It was noted during experimental results the formation of regions of low porosity in the heat-treated coatings, indicating regions of column bridging/necking. These results show decreasing porosity with increasing temperatures, consistent with higher measured elastic modulus.

Figure 5:
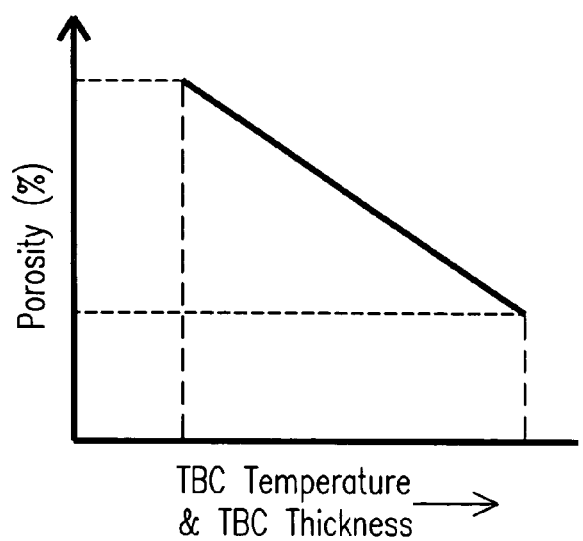
FIG. 5 is a graph that illustrates an exemplary functional relationship that may be used by a system embodying aspects of the present invention for correlating a measured micro-structural characteristic to estimate a TBC exposure temperature.

In operation quantitative analysis regarding porosity information, (e.g., volumetric porosity in the coating, and/or porosity gradient versus thickness) may be performed for as-deposited (virgin TBC coatings) and aged TBC coatings by monitoring micro-structural changes that develop over time due to operational-encountered heating. FIG. 5 is a graph that illustrates an exemplary functional relationship that may be used for correlating a measured micro-structural characteristic (e.g., volumetric porosity in a particular section of the coating or local porosity at a given TBC thickness) to a TBC exposure temperature. This may be useful to determine a thermal gradient across the TBC, which, for example, may indicate a local heat flux to which the component has been subjected, as opposed to a flux value derived from a theoretical thermal model. It will be appreciated that this would provide valuable information to a component designer. For example, this may allow the designer to better map the heat loads that the component actually has to withstand in operation. This may be used for validating or updating the thermal model used by the designer to predict the heat flux at a given component location. Moreover, aspects of the present invention may be used for estimating TBC surface temperatures of service-run parts. It is contemplated that this capability will be conducive to more consistently and more accurately identifying the role of TBC over-temperature conditions as a cause of TBC degradation that could ultimately lead to spallation of the TBC.

Aspects of the invention can also be embodied as computer readable code on a computer readable medium. The computer readable medium is any data storage device that can store data, which thereafter can be read by a computer system. Examples of computer readable medium include read-only memory, random-access memory, CD-ROMs, DVDs, magnetic tape, optical data storage devices. The computer readable medium can also be distributed over network coupled computer systems so that the computer readable code is stored and executed in a distributed fashion.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for example, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

An apparatus for making, using or selling the invention may be one or more processing systems including, but not limited to, a central processing unit (CPU), memory, storage devices, communication links and devices, servers, I/0 devices, or any sub-components of one or more processing systems, including software, firmware, hardware or any combination or subset thereof, which embody the invention as set forth in the claims.

User input may be received from the keyboard, mouse, pen, voice, touch screen, or any other means by which a human can input data to a computer, including through other programs such as application programs.

One skilled in the art of computer science will easily be able to combine the software created as described with appropriate general purpose or special purpose computer hardware to create a computer system or computer subsystem embodying the method of the invention.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

We claim as our invention:

1. A method for non-destructively inspecting and characterizing micro-structural features in a thermal barrier coating on an in-service component of a power generating turbine, wherein said micro-structural features define pores and cracks, if any, in said thermal barrier coating, said micro-structural features having characteristics at least in part based on a type of process used for developing said thermal barrier coating and affected by thermal loads to which a thermal barrier coating is exposed during operation of the power generating turbine, said method comprising:

selecting an in-service component of the power generating turbine to be monitored over a period of time;

detecting micro-structural features in a thermal barrier coating of the selected in-service component, wherein the detecting of the micro-structural features is based on energy transmitted through said coating, wherein the thermal barrier coating is expected to encounter heat flux values based on a theoretical thermal model configured to map heat flux values for a plurality of locations of the in-service component;

processing said transmitted energy to generate data representative of said micro-structural features;

processing the data representative of said micro-structural features to determine at least one of the following: volumetric porosity information for the thermal barrier coating and information regarding variation in the characteristics of said micro-structural features over a thickness of said thermal barrier coating;

based on the results of said data processing, generating information regarding at least one of the following: a present condition of the thermal barrier coating and a future likely condition of the thermal barrier coating;

generating an image indicative of the information regarding the present condition of the thermal barrier coating and/or the future likely condition of the thermal barrier coating;

validating with the information indicated by the generated image whether heat flux values based on the theoretical thermal model correspond to actual heat flux values encountered by the in-service component during operation of the power generating turbine;

based on the actual heat flux values encountered by the in-service component, estimating a remaining operational life of the thermal barrier coating, said estimating further comprising relating representative data of the thermal barrier coating having been exposed to thermal loads relative to representative data of a virgin coating; and generating a representation indicative of the remaining operational life of the thermal barrier coating.

2. The method of claim 1 wherein the detecting comprises performing a computerized micro-tomography scan of the thermal barrier coating, and the representative data comprises three-dimensional data of said micro-structural features based on the computerized micro-tomography scan.

3. The method of claim 2 further comprising processing said three-dimensional data to form a three-dimensional image of said micro-structural features, configuring said three-dimensional image with sufficient resolution to enable a user to visually asses at least one of the following: the volumetric porosity information and the variation in the characteristics of said micro-structural features over the thickness of said thermal barrier coating.

4. The method of claim 2 further comprising processing said three-dimensional data to quantitatively assess at least one of the following: the volumetric porosity information for said thermal barrier coating and the variation in the characteristics of said micro-structural features over the thickness of said thermal barrier coating.

5. The method of claim 1 wherein the detecting of the micro-structural features is selected from the group consisting of detecting based on computerized micro-tomography scanning, detecting based on small angle neutron scattering, and detecting based on ultra-small angle x-ray scattering.

6. The method of claim 1 further comprising correlating the variation in the characteristics of said micro-structural features over the thickness of said thermal barrier coating to a predefined model to estimate a level of thermal load to which the thermal barrier coating has been exposed.

7. The method of claim 6 further comprising estimating duration of exposure to the estimated level of thermal load.

8. The method of claim 1 further comprising correlating the volumetric porosity information to a predefined model to estimate a level of thermal load to which the thermal barrier coating has been exposed.

9. The method of claim 1 wherein the type of process used for developing said thermal barrier coating is selected from the group consisting of a plasma sprayed process, an electron beam physical vapor deposition process and a chemical vapor deposition process.

10. A method for non-destructively inspecting and characterizing micro-structural features in a thermal barrier coating on an in-service component of a power generating turbine, wherein said micro-structural features define pores and cracks, if any, in said thermal barrier coating, and said micro-structural features have characteristics at least in part based on a type of process used for developing said thermal barrier coating and affected by operational thermal loads to which a thermal barrier coating is exposed during operation of the power generating turbine, said method comprising:

selecting an in-service component of the power generating turbine to be monitored over a period of time;

detecting micro-structural features in a thermal barrier coating of the selected in-service component, wherein the detecting of the micro-structural features is based on energy transmitted through said coating, wherein the thermal barrier coating is expected to encounter heat flux values based on a theoretical thermal model configured to map heat flux values for a plurality of locations of the in-service component;

processing said transmitted energy to generate data representative of said micro-structural features;

processing the data representative of said mircro-structural features to determine at least one of the following: volumetric porosity information for the thermal barrier coating, and information regarding variation in the characteristics of said micro-structural features over a thickness of said thermal barrier coating;

based on the results of said data processing, estimating a level of thermal load to which the thermal barrier coating has been exposed;

generating a signal indicative of the information regarding the level of thermal load to which the thermal barrier coating has been exposed;

validating with the information indicated by the generated signal whether heat flux values based on the theoretical thermal model correspond to actual heat flux values encountered by the in-service component during operation of the power generating turbine;

based on the actual heat flux values encountered by the in-service component, estimating a remaining operational life of the thermal barier coating, said estimating further comprising relating representative data of the thermal barrier coating having been exposed to thermal loads relative to representative data of a virgin coating; and generating a representation indicative of the remaining operational life of the thermal barrier coating.

11. the method of claim 10 further comprising estimating time duration of exposure to the estimated level of thermal load.

12. The method of claim 10 wherein the estimating of the level of thermal load to which the thermal barrier coating has been exposed comprises correlating the variation in the characteristics of said micro-structural features over the thickness of said thermal barrier coating to a predefined model.

13. The method of claim 10 wherein the estimating of the level of thermal load to which the thermal barrier coating has been exposed comprises correlating the volumetric porosity information to a predefined model.

14. The method of claim 10 wherein the detecting comprises performing a computerized micro-tomography scan of the coating, and the representative data comprises three-dimensional data of said micro-structural features.

15. The method of claim 14 further comprising processing said three-dimensional data to form a three-dimensional image of said micro-structural features, configuring said three-dimensional image with sufficient resolution to enable a user to visually assess at least one of the following: the volumetric porosity information for said thermal barrier coating and the variation in the characteristics of said micro-structural features over the thickness of said thermal barrier coating.

16. The method of claim 14 further comprising processing said three-dimensional data to quantitatively assess at least one of the following: the volumetric porosity information for said thermal barrier coating and the variation in the characteristics of said micro-structural features over the thickness of said thermal barrier coating.

17. The method of claim 10 wherein the detecting of the micro-structural features is selected from the group consisting of detecting based on computerized micro-tomography, detecting based on small angle neutron scattering, and detecting based on ultra-small angle x-ray scattering.

18. the method of claim 10 wherein the type of process used for developing said thermal barrier coating is selected from the group consisting of a plasma sprayed process and physical and chemical vapor deposition process.

* * * * *